Figure 1:
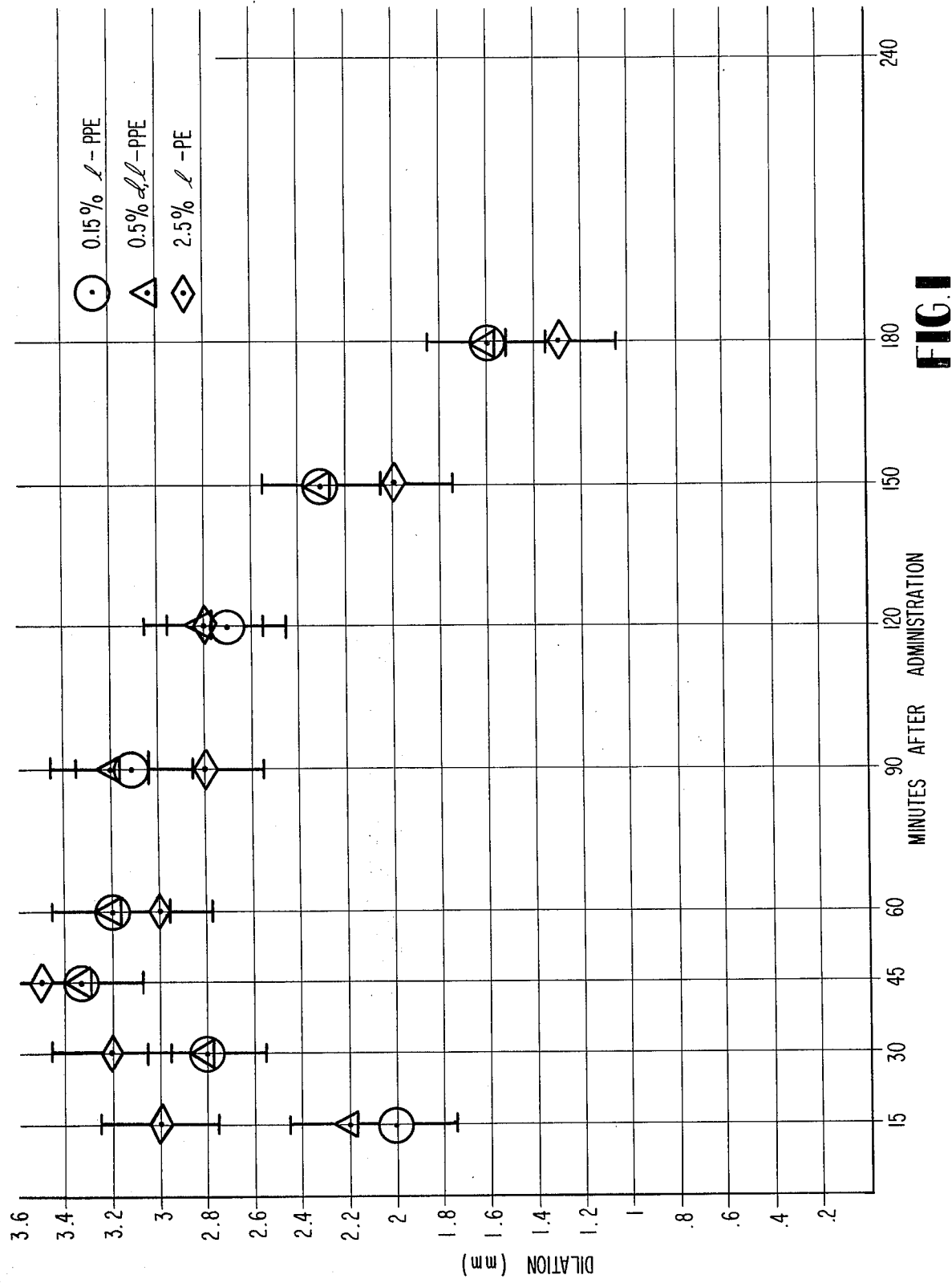

United States Patent
Bodor et al.

[11] 3,966,749
[45] June 29, 1976

[54] NOVEL SYNTHESIS OF OPTICALLY ACTIVE M-ACYLOXY-α-[(METHYLAMINO)METHYL]BENZYL ALCOHOLS, THE PHARMACEUTICALLY ACCEPTABLE ACID ADDITION SALTS THEREOF AND INTERMEDIATE USEFUL IN THE PREPARATION THEREOF

[75] Inventors: Nicolae S. Bodor; Sun-Shine Yuan, both of Lawrence, Kans.

[73] Assignee: Interx Research Corporation, Lawrence, Kans.

[22] Filed: Feb. 10, 1975

[21] Appl. No.: 548,606

[52] U.S. Cl. .................. 260/295 R; 260/570.7
[51] Int. Cl.² .......................... C07D 213/02
[58] Field of Search ............... 260/295 R, 570.7

[56] References Cited
UNITED STATES PATENTS

| 3,542,874 | 11/1970 | Keizer et al. ............ 260/570.7 OH |
| 3,641,152 | 2/1972 | Shavel, Jr. et al. ........ 260/570.7 OH |
| 3,825,583 | 7/1974 | Hussain et al. .................. 424/311 |

FOREIGN PATENTS OR APPLICATIONS

| 1,178,721 | 1/1970 | United Kingdom ............ 260/570.7 |

OTHER PUBLICATIONS

Elderdield, "Heterocyclic Compounds," vol. 5, p. 391, (1957).
Morrison et al., Organic Chemistry, p. 593, (1959).

*Primary Examiner*—Norman A. Drezin
*Attorney, Agent, or Firm*—Charles N. Blitzer

[57] ABSTRACT
Optically and therapeutically active compounds of the formula:

(I)

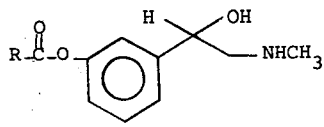

wherein R represents a member selected from the group consisting of a straight or branched alkyl group of from one to twenty carbon atoms ($C_1$–$C_5$ being preferred), an ethoxycarbonyl group, a benzyloxycarbonyl group, a phenyl group, an

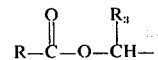

group, wherein R is as defined above and $R_3$ is a member selected from the group consisting of a hydrogen atom, a methyl group and a phenyl group, and a 2-, 3-, or 4-pyridyl group, or the HX salts thereof, wherein X represents a pharmaceutically acceptable acid addition salt anion, are prepared using optically active m-hydroxy-α-[(methylamino)-methyl]benzyl alcohol (phenylephrine).

The compounds prepared by the process of this invention find therapeutic applicaton to warm-blooded animals (e.g., humans) in the management of asthma, nasal congestion and as decongestants, vasoconstrictors, mydriatic agents, and anti-glaucomatous agents in the practice of opthalmology.

Upon administration, these compounds will enzymatically "cleave," thus releasing optically active phenylephrine (m-hydroxy-α-[(methylamino)methyl]benzyl alcohol, the therapeutically active moiety thereof.

13 Claims, 1 Drawing Figure

NOVEL SYNTHESIS OF OPTICALLY ACTIVE M-ACYLOXY-α-[(METHYLAMINO)METHYL]-BENZYL ALCOHOLS, THE PHARMACEUTICALLY ACCEPTABLE ACID ADDITION SALTS THEREOF AND INTERMEDIATE USEFUL IN THE PREPARATION THEREOF

BACKGROUND OF THE INVENTION

1. Field of the Invention

The present invention is directed to certain esters of m-hydroxy-α-[(methylamino)methyl]benzyl alcohols, their pharmaceutically acceptable acid addition salts and certain intermediates useful in the preparation thereof. More particularly, the instant invention is directed to a novel synthesis for preparing the optically active (hereinafter R) or racemate form of the above-identified compounds.

Upon administration, these compounds will enzymatically "cleave" and release optically active m-hydroxy-α-[(methylamino)methyl]benzyl alcohol (phenylephrine), the therapeutically active moiety thereof.

2. Description of the Prior Art

U.S. Pat. No. 3,825,583 — Hussain and Truelove, discloses and claims an ester of m-hydroxy-α-[(methylamino)methyl]benzyl alcohol, namely, m(3-)-pivaloxy-α-[methylamino)methyl]benzyl alcohol.

A review of the manner in which this compound is prepared readily reveals that a racemic mixture (a mixture containing both the biologically active and the biologically non-active isomer) is obtained. Since the R isomer is the only isomer exhibiting therapeutic activity, to date (R)-m-pivaloxy-α-[(methylamino)methyl]benzyl alcohol is normally administered in the form of a racemic mixture as the means to separate the optically active form from the racemic mixture is quite time consuming and expensive.

Therefore, a need exists for a means to synthesize the optically active form of certain m-aceyloxy-α-[(methylamino)methyl]benzyl alcohols of which m-pivaloxy-α-[(methylamino)methyl]benzyl alcohol is so among and thus avoid the need to (1) first obtain a racemic mixture, and (2) optionally, resolve the racemic mixture into the optically active isomer for administration or administer the racemic mixture, per se.

In addition to the foregoing, it is obviously apparent that since only the active isomer of the compounds described herein is therapeutically active, the dosage amount of a racemic mixture containing the same required to achieve therapeusis is much greater than that which would be required if the optically active form were administered, per se. Thus, an ancillary need exists for a means to synthesize the optically active isomer, per se, for the sake of minimizing the therapeutic dose required as well as to avoid any toxic reactions which may occur.

SUMMARY OF THE INVENTION

It is, therefore, the primary object of the present invention to synthesize the optically active form of certain m-acyloxy-α-[(methylamino)methyl]benzyl alcohols as described herein, which upon administration to a warm-blooded animal (e.g., human) will enzymatically "cleave" to release optically active phenylephrine, the therapeutically active moiety thereof.

It is another object of the present invention to synthesize the above-described optically active forms so as to enable therapeusis to be achieved with a lesser dose of the optically active form over a racemic mixture containing the same.

These and other obvious objects are achieved via the synthesis scheme set out below.

(I) 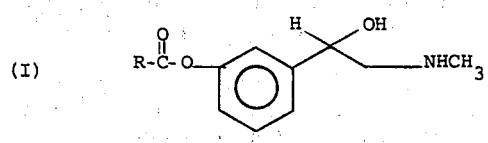

wherein R represents a member selected from the group consisting of a straight or branched alkyl group of from one to 20 carbon atoms ($C_1$–$C_5$ being preferred), an ethoxycarbonyl group, a benzyloxycarbonyl group, a phenyl group, an

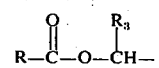

group, wherein R is defined as above and $R_3$ represents a member selected from the group consisting of a hydrogen atom, a methyl group and a phenyl group, and a 2-, 3-, or 4-pyridyl group, or the HX salts thereof, and wherein X represents a pharmaceutically acceptable acid addition salt anion derived from the corresponding acid (e.g., chloride, bromide, sulfate, sulfonate, phosphate, nitrate, acetate, propionate, succinate, glycolate, stearate, lactate, tartrate, citrate, ascorbate, parmoate, maleate, hydroxymaleate, phenylacetate, glutamate, benzoate, salicylate, sulfonilate, fumarate, toluenesulfonate, etc.) are prepared by:

1. reacting optically active phenylephrine with an excess of a carbonyl compound of the formula: $R_1$—CO—$R_2$, wherein $R_1$ and $R_2$ which can be the same or different and represent a member selected from the group consisting of a hydrogen atom, a $C_1$–$C_{10}$ alkyl group, and a di($C_1$–$C_2$)alkylamino($C_1$–$C_{10}$)alkyl group, or wherein $R_1$ and $R_2$ together with the carbonyl group to which they are attached can form a member selected from the group consisting of a $C_5$–$C_7$ cycloalkanone group (pentanone, hexanone, or heptanone) and a substituted or unsubstituted N- or O-heterocyclic(-$C_5$–$C_7$) alkanone group (e.g., piperidone, pyrrolidone, N-methylpiperidone, or N-methylpyrrolidone, etc.), wherein said substituent is a $C_1$–$C_2$ alkyl group, either in the presence of a dehydrating agent selected from the group consisting of, but not limited to an alkaline earth metal carbide (calcium carbide, magnesium carbide, etc.), a molecular sieve of from 4 to 5 A, calcium chloride, magnesium sulfate, and sodium sulfate, or in the presence of a conventional inert aromatic hydrocarbon solvent (e.g., benzene, toluene, xylene, etc.) plus an organic or inorganic acid catalyst (e.g., p-toluenesulfonic acid, sulfoscalicyclic acid, benzenesulfonic acid, sulfuric acid, hydrochloric acid, etc.) to eliminate the water formed as an azeotropic mixture, said steps being carried out at a temperature of from 20° to 140° C (preferably, however, at the boiling point of the solvent or solvent mixture employed), standard pressure, and for a period of time ranging from 2 to 48 hours, whereby intermediate:

(II) 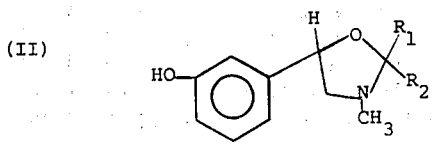

wherein $R_1$ and $R_2$ are defined as above is formed:

2. reacting with intermediate of step (1) with a number selected from the group consisting of an M-hydroxide, an M-hydride, and an M-alkoxide, wherein M represents a member selected from the group consisting of an alkali metal, an alkaline earth metal, and thallium (e.g., NaOH, KOH, Ca(OH)$_2$, Mg(OH)$_2$, Ba(OH)$_2$, NaH, CaH$_2$, NaOCH$_3$, NaOC$_2$H$_5$, NaOC$_3$H$_7$, TlOC$_2$H$_5$, etc.) in the presence of an inert organic solvent selected from the group consisting of an aliphatic hydrocarbon solvent of from five to 10 carbon atoms (e.g., pentane, hexane, heptane,, octane, decane, etc.), an aromatic hydrocarbon solvent (e.g., benzene, toluene, xylene, etc.), and C$_1$–C$_4$ aliphatic alcohol (methanol, ethanol, propanol, butanol), a conventional ether (e.g., diethyl ether, tetrahydrofuran, dioxane, etc.) and dimethylformamide, etc., said step being carried out at room temperature, standard pressure, and for a period of time ranging from 1 to 24 hours, whereby the intermediate:

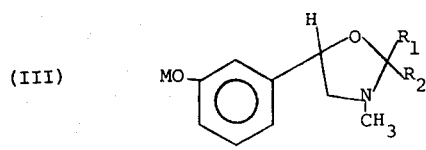

(III)

wherein M, $R_1$, and $R_2$ are defined above is formed;

3. reacting the intermediate of step (2) with a stoichiometric amount of an acyl halide of the formula: R—CO—Y, wherein R is defined as above and Y represents a halogen atom (chlorine, bromine, iodine) in the presence of an inert organic solvent selected from the group consisting of an aliphatic hydrocarbon solvent of from five to 10 carbon atoms, an aromatic hydrocarbon solvent (e.g., benzene, toluene, xylene, etc.), methanol, propanol, butanol, a conventional ether (e.g., diethyl ether, tetrahydrofuran, dioxane, etc.), or dimethylformamide, said step being carried out at room temperature, standard pressure, and for a period of time ranging from 1 to 24 hours, whereby the intermediate:

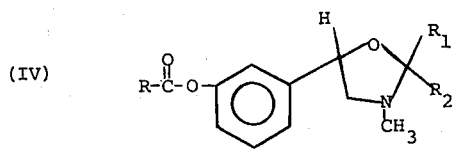

(IV)

wherein R, $R_1$, and $R_2$ are defined as above is formed; and 4. cleaving the $R_1$—CO—$R_2$ moiety of the intermediate from step (3) in an organic inert solvent selected from the group consisting of an aliphatic hydrocarbon solvent of from five to 10 carbon atoms, an aromatic hydrocarbon solvent (e.g., benzene, toluene, xylene, etc.), a C$_1$–C$_4$ aliphatic alcohol, a conventional ether (diethyl ether, tetrahydrofuran, dioxane, etc.), and dimethylformamide and further in the presence of a stoichiometric or excess amount of water and a catalytic amount (normally but not absolutely, 0.01–1.0% of the stoichiometric amount) of an HX acid, wherein X is defined as above, said step being carried out at a temperature of from 20° to 100°C, standard pressure, and for a period of time of from 1 to 24 hours, whereby the free base of formula (I) is obtained; and 5. optionally, replacing the catalytic amount of the HX acid in step (4) with the stoichiometric amount of the same, whereby the HX salt of the free base of the compound represented by formula (I) is obtained.

The compounds prepared by the process of this invention find therapeutic application to warm-blooded animals (e.g., humans) in the management of asthma, nasal congestion, and as decongestants, vasoconstrictors, mydriatic agents, and anti-glaucomatous agents in the practice of ophthalmology. Upon administration, they will enzymatically "cleave" and release phenylephrine, the therapeutically active moiety thereof.

At this juncture, it should be emphasized that the intermediate products formed in steps (1), (2), and (3) are considered novel by the present inventors and specific for the process described and claimed herein, or any process equivalent thereto. As such, these intermediates are considered part and parcel of the overall invention described in the instant application.

In addition, a number of solvents and acid catalysts have been described for purposes of exemplification. However, it is apparent that any solvent or acid catalyst not described but serving the same purpose as required by the present inventors is included within the scope of the instant invention.

Finally, it is obvious that the instantly described procedure can be employed equally as well in the synthesis of racemic mixtures containing the above-described compound by simply substituting racemic phenylephrine for optically active phenylephrine in step (1). As such, the scope of this invention is extended to include this feature as well.

Without further elaboration, it is believed that one of ordinary skill in the art can, using the preceding description, utilize the instant invention to its fullest extent. Consequently, the following preferred specific embodiments are, therefore, to be construed as merely illustrative and not limitative of the remainder of the specification and claims in any way whatsoever.

EXAMPLE I

PREPARATION OF OPTICALLY ACTIVE m-(TRIMETHYLACETOXY)-α-[(METHYLAMINO)METHYL]BENZYL ALCOHOL HYDROCHLORIDE (R)-phenylephrine (9.0 g, 0.05 mole), acetone (1 liter) and calcium carbide (4.0 g, 0.06 mole) were heated together at reflux with stirring for 24 hours. The solid material formed was filtered off and the filtrate was concentrated in vacuo. The residue was crystallized in an acetone-hexane mixture to give 7.0 g of (R)-2,2,3-trimethyl-5-(m-hydroxyphenyl)-1,3-oxazolidine, 70% yield. mp 118°–120° C, $\alpha_D^{25°} = -17.9°$ (CH$_3$OH), ir (KBr): 2980, 2860, 2700, 1600, 1450, 1260 and 1120 cm$^{-1}$. nmr (CD$_3$COCD$_3$): δ 7.4–6.6 (m, 4H), 5.2 (b, 1H), 5.0 (t, 1H, J = 7Hz), 3.3 (dd, 1H, J = 7 and 9Hz), 2.7 (dd, 1H, J = 7 and 9Hz), 2.4 (s, 3H) and 1.3 (s, 6H) ppm.

Anal. Calcd for C$_{12}$H$_{17}$NO$_2$: C, 69.6; H, 8.2; N, 6.8. Found: C, 70.3; H, 8.4; N, 6.7.

To a solution of the (R)-2,2,3-trimethyl-5-(m-hydroxyphenyl)-1,3-oxazolidine previously obtained (1.32 g, 6.38 mmole) in 60 ml of ether, there was added thallous ethoxide (1.59 g, 6.38 mmole) and the mixture was stirred at room temperature for 1 hour.

Pivalyl chloride (0.79 ml, 6.38 mmole) was then added and stirring was maintained for two additional hours. The solid material formed in the reaction was filtered and the filtrate (this solution was usually used directly in the next reaction without evaporation) was evaporated to dryness to give 1.8 g of an oily product, (R)-2,2,3-trimethyl-5-(m-trimethylacetoxyphenyl)-1,3-oxazolidine, 95% yield. $\alpha_D^{25°} = -10.6°$ ($C_2H_5OH$). ir(neat): 2960, 1760, 1610, 1590, 1480, 1450, 1370, 1360, 1260, 1230, 1140 and 1105 cm$^{-1}$. nmr ($CCl_4$): δ 7.4–6.8 (m, 4H), 5.0 (t, 1H, J = 7Hz), 3.3 (dd, 1H, J = 7 and 9Hz), 2.8 (dd, 1H, J = 7 and 9Hz), 2.3 (s, 3H), 1.4 (s, 9H) and 1.3 (s, 6H) ppm.

The filtrate obtained in the previous reaction containing (R)-2,2,3-trimethyl-5-(m-trimethylacetoxyphenyl)-1,3-oxazolidine (1.8 g, 6.2 mmole) in 60 ml of ether was treated with hydrogen chloride gas until the solution was no longer turbid. This mixture was then evaporated to dryness and the residue was dissolved in a small amount of ethanol and then diluted with hexane. The hydrolysis and crystallization took place in the solution to give 1.2 g of the final product, (R)-m-(trimethylacetoxy)-α-[methylamino)methyl]benzyl alcohol hydrochloride, 70% yield. mp 128°–130° C, $\alpha_D^{25°} = -36.7°$ ($C_2H_5OH$). ir (KBr): 3370, 2690, 2795, 2420, 1750, 1610, 1590, 1460, 1240 and 1110 cm$^{-1}$. nmr ($CD_3COCD_3$. $D_2O$): δ7.5–6.8 (m, 4H), 5.3 (dd, 1H, J = 5 and 10Hz), 3.8 (b, 3H), 3.4 (m, 2H), 2.9 (s, 3H) and 1.4 (s, 9H) ppm.

Anal. Calcd for $C_{14}H_{22}NO_3Cl$: C, 58.4; H, 7.7; N, 4.9. Found: C, 58.4; H, 7.7; N, 4.6.

The remaining compounds of formula (I) can be prepared with similar success by substituting the generically or specifically described reactants and/or operating conditions of this invention for those used in the preceding example. Similarly, this process can be used to prepare the enantiomeric(S)-isomers or the racemic (R,S)-isomers as well.

EXAMPLE II

HYDROLYSIS (CLEAVAGE) OF OPTICALLY ACTIVE
m-(TRIMETHYLACETOXY)-α-[(METHYLAMINO)METHYL]BENZYL ALCOHOL HYDROCHLORIDE TO OPTICALLY ACTIVE PHENYLEPHRINE
(m-HYDROXY-α-[(METHYLAMINO)METHYL]-BENZYL ALCOHOL)

The following study clearly evidences the fact that the compounds of the instant invention hydrolytically "cleave," thus releasing (R)-phenylephrine hydrochloride, the therapeutic moiety of the initial compound.

(R)-m-(trimethylacetoxy)-α-[(methylamino)methyl]benzyl alcohol hydrochloride obtained from Example I (1.0 g) was dissolved in 10 ml of methanol containing 1 ml of concentrated hydrochloric acid. The resulting solution was then refluxed for 24 hours, and subsequently, the solvent was then removed in vacuo to give 0.7 g (90% yield) of (R)-phenylephrine as determined by conventional optical activity determination procedures. $\alpha_D^{25°} = 47.0°$ (Lit. $\alpha_D^{25°} = -46.2$, Dictionary of Organic Compounds. 4th Ed. Oxford University Press, 1965).

EXAMPLE III

MYDRIATIC STUDIES

Standard doses of 50 μ1 of the following isotonic solutions were applied onto male and female rabbit eyes: 0.15% of (R)-m-(trimethylacetoxy)-α-[(methylamino)methyl]benzyl alcohol hydrochloride (l-PPE, this invention); 0.5% of a racemic mixture of m-pivaloxy-α-[(methylamino)methyl]benzyl alcohol hydrochloride (d,l-PPE) — U.S. Pat. No. 3,825,583; and 2.5% of (R)-phenyleprhine hydrochloride (l-PE). All of the compounds tested elicited the same mydriatic response as can be seen from a review of FIG. 1 accompanying the instant application. Thus, it is clearly established that the compounds of this invention easily elicit a mydriatic response at a much lesser dosage rate than that observed for its closest competitors (m-pivaloxy-α-[(methylamino)methyl]benzyl alcohol hydrochloride) or phenylephrine hydrochloride, per se.

By following the above procedure, equivalent mydriatic responses will be observed for the remaining compounds of formula (I).

The compounds prepared by the process of the instant invention can be used by the pharmaceutical and/or veterinary arts for the treatment of glaucoma, bronchial asthma, and nasal decongestion associated with hay fever and allergic rhinitis in warmblooded animals (e.g., humans) in a variety of pharmaceutical preparations as described in U.S. Pat. No. 3,825,583.

As for the therapeutic dose required of the compounds prepared or the process of the instant invention, while dosage limitations will naturally vary with the size and needs of the individual treated, normally, the dosage range will mimic that described for the compound m-pivaloxy-α-[(methylamino)methyl]benzyl alcohol as described in U.S. Pat. No. 3,825,583.

From the foregoing description, one of ordinary skill in the art can easily ascertain the essential characteristics of this invention, and without departing from the spirit and scope thereof, can make various changes and/or modifications of the invention to adapt it to various usages and conditions. As such, these changes and/or modifications are properly, equitably, and intended to be, within the full range of equivalence of the following claims.

What we claim is:

1. A method for preparing an optically and therapeutically active (m-acyloxy-α-[(methylamino)methyl]-benzyl alcohol of the formula:

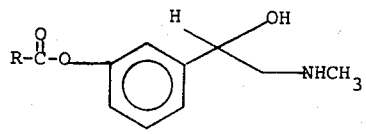

wherein R represents a member selected from the group consisting of a straight or branched alkyl group or from one to twenty carbon atoms, an ethoxycarbonyl group, a benzyloxycarbonyl group, a phenyl group, an

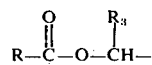

group, wherein R is as defined above and $R_3$ is a member selected from the group consisting of a hydrogen atom, a methyl group and a phenyl group, and a 2-, 3-, or 4-pyridyl group, or the HX salts thereof, wherein X represents a pharmaceutically acceptable acid addition salt anion which consists essentially of 1. reacting optically active phenylephrine with an excess of a carbonyl compound of the formula: $R_1—CO—R_2$, wherein $R_1$ and $R_2$ which can be the same or different and represent a member selected from the group consisting of a hydrogen atom, a $C_1-C_{10}$ alkyl group, and a $di(C_1-C_2)alkylamino(C_1-C_{10})alkyl$ group, or wherein $R_1$ and $R_2$ together with the carbonyl group to which they are attached can form a member selected from the group consisting of a $C_5-C_7$ cycloalkanone group and a substituted or unsubstituted N- or O-heterocyclic $(C_5-C_7)$ alkanone group, wherein said substituent is a $C_1-C_2$ alkyl group, either in the presence of a dehydrating agent selected from the group consisting of an alkaline earth metal carbide, a molecular sieve of from 4 to 5 A, calcium chloride, magnesium sulfate, and sodium sulfate, or in the presence of a conventional inert aromatic hydrocarbon solvent plus an organic or inorganic acid catalyst to eliminate the water formed as an azeotropic mixture, said step being carried out at a temperature of from 20° to 140° C, standard pressure, and for a period of time ranging from 2° to 2 to 48 hours, whereby the intermediate;

(II) 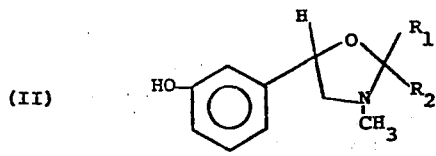

wherein $R_1$ and $R_2$ are defined as above is formed;

2. reacting the intermediate of step (1) with a member selected from the group consisting of an M-hydroxide, an M-hydride, and an M-alkoxide, wherein M represents a member selected from the group consisting of an alkali earth metal, an alkaline earth metal and thallium in the presence of an inert organic solvent selected from the group consisting of an aliphatic hydrocarbon solvent or from five to 10 carbon atoms, an aromatic hydrocarbon solvent, and $C_1-C_4$ aliphatic alcohol, a conventional ether and dimethylformamide, said step being carried out at room temperature, standard pressure, and for a period of time ranging from 1 to 24 hours, whereby the intermediate:

(III) 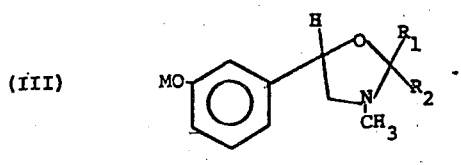

wherein M, $R_1$, and $R_2$ are defined above is formed;

3. reacting the intermediate of step (2) with a stoichiometric amount of an acyl halide of the formula: R—CO—Y, wherein R is defined as above and Y represents a halogen atom in the presence of an inert organic solvent selected from the group consisting of an aliphatic hydrocarbon solvent of from five to 10 carbon atoms, an aromatic hydrocarbon solvent, methanol, propanol, butanol, a conventional ether, and dimethylformamide, said step being carried out at room temperature, standard pressure, and for a period of time ranging from 1 to 24 hours, whereby the intermediate:

(IV) 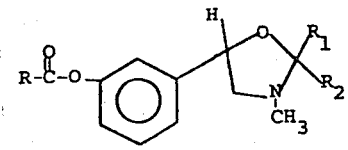

wherein R, $R_1$, and $R_2$ are defined as above is formed; and 4. cleaving the $R_1—CO—R_2$ moiety of the intermediate from step (3) in an organic inert solvent selected from the group consisting of an aliphatic hydrocarbon solvent of from five to ten carbon atoms, an aromatic hydrocarbon solvent, a $C_1-C_4$ aliphatic alcohol, a conventional ether, and dimethyl formamide and further in the presence of a stoichiometric or excess amount of water and a catalytic amount of an HX acid, wherein X is defined as above, said step being carried out at a temperature of from 20° to 100° C, standard pressure, and for a period of time of from 1 to 24 hours, whereby the free base of formula (I) is obtained.

2. The process of claim 1, wherein in step (4), a stoichiometric amount of said HX acid is employed to obtain the pharmaceutically acceptable acid addition salt of the compound of formula (I).

3. The method of claim 1, wherein in step (4), said catalytic amount of said HX acid is in the range of from 0.01 to 1.0% of the stoichiometric amount.

4. The amount of claim 1, wherein in step (1), said step is carried out at a temperature equivalent to the boiling point of the solvent or solvent mixture employed.

5. The method of claim 1, wherein in step (1), said carbonyl compound is a member selected from the group consisting of pentanone, hexanone, heptanone, piperidone, pyrrolidone, N-methylpiperidone, and N-methylpyrrolidone.

6. The method of claim 1, wherein in step (1), said aromatic hydrocarbon solvent is a member selected from the group consisting of benzene, toluene, and xylene.

7. The method of claim 1, wherein in step (1), said acid catalyst is a member selected from the group consisting of p-toluene-sulfonic acid, sulfosalicylic acid, benzenesulfonic acid, sulfuric acid, and hydrochloric acid.

8. The method of claim 1, wherein in step (2), said metal hydroxide, metal hydride, or metal alkoxide is a member selected from the group consisting of sodium hydroxide, potassium hydroxide, calcium hydroxide, magnesium hydroxide, barium hydroxide, sodium hydride, calcium hydride, sodium methoxide, sodium ethoxide, sodium propoxide, and thallous ethoxide.

9. The method of claim 1, wherein in step (2), said inert organic solvent is a member selected from the group consisting of pentane, hexane, heptane, octane, nonane, decane, benzene, toluene, xylene, methanol, ethanol, butanol, propanol, diethyl ether, tetrahydrofuran, dioxane and dimethylformamide.

10. The method of claim 1, wherein in step (3), said inert organic solvent is a member selected from the group consisting of pentane, hexane, heptane, octane, nonane, decane, benzene, toluene, xylene, methanol, propanol, butanol, diethyl ether, tetrahydrofuran, dioxane, and dimethylformamide.

11. The method of claim 1, wherein in step (4), said HX acid is a member selected from the group consisting of hydrochloric acid, hydrobromic acid, sulfuric acid, sulfamic acid, phosphoric acid, nitric acid, acetic acid, propionic acid, succinic acid, glycollic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfonilic acid, fumaric acid and toluenesulfonic acid.

12. The method of claim 1, wherein in formula (I), R represents a straight or branched alkyl group of from one to five carbon atoms.

13. The method of claim 1, wherein in step (1), optically active phenylephrine is replaced with racemic phenylephrine, thus yielding racemic m-acyloxy-α-[(methylamino)methyl]benzyl alcohol.

* * * * *